(12) United States Patent
Murai et al.

(10) Patent No.: US 8,148,573 B2
(45) Date of Patent: Apr. 3, 2012

(54) POLYFLUORALKANE CARBOXYLIC ACID (OR ITS SALT) AND PROCESS FOR PRODUCING THE SAME

(75) Inventors: Daisuke Murai, Ibaraki (JP); Takashi Enokida, Ibaraki (JP); Seiichiro Murata, Ibaraki (JP)

(73) Assignee: Unimatec Co., Ltd., Tokyo (JP)

( * ) Notice: Subject to any disclaimer, the term of this patent is extended or adjusted under 35 U.S.C. 154(b) by 502 days.

(21) Appl. No.: 12/310,641

(22) PCT Filed: Jul. 17, 2007

(86) PCT No.: PCT/JP2007/064074
§ 371 (c)(1),
(2), (4) Date: Mar. 2, 2009

(87) PCT Pub. No.: WO2008/026393
PCT Pub. Date: Mar. 6, 2008

(65) Prior Publication Data
US 2011/0251427 A1    Oct. 13, 2011

(30) Foreign Application Priority Data
Aug. 29, 2006 (JP) ................ 2006-231587

(51) Int. Cl.
C07C 51/15 (2006.01)
C07C 53/21 (2006.01)
(52) U.S. Cl. .................. 562/552; 562/605
(58) Field of Classification Search ............ 562/552, 562/605
See application file for complete search history.

(56) References Cited

U.S. PATENT DOCUMENTS

| 4,380,618 A | 4/1983 | Khan et al. |
| 5,763,552 A | 6/1998 | Feiring et al. |

FOREIGN PATENT DOCUMENTS

| DE | 21 20 364 A1 | 11/1971 |
| EP | 0 818 490 A2 | 1/1998 |
| GB | 1 509 404 A | 5/1978 |
| JP | 08-231462 | 9/1996 |

OTHER PUBLICATIONS

Supplementary European Search Report from corresponding European Application No. 07790836.6 dated Dec. 10, 2010, 5 pages.

*Primary Examiner* — Sikarl Witherspoon
(74) *Attorney, Agent, or Firm* — Brinks Hofer Gilson & Lione

(57) ABSTRACT

A polyfluoroalkane carboxylic acid represented by the following general formula:

$$C_nF_{2n+1}(CH_2CF_2)_m(CF_2CF_2)_{l-1}CF_2COOM$$

(M: an alkali metal, a $NH_4$ group or H; n: an integer of 1 to 6; m: an integer of 1 to 4; and l: 1 or 2) can be produced by hydrolysis reaction of polyfluoroalkane carboxylic acid fluoride represented by the following general formula:

$$C_nF_{2n+1}(CH_2CF_2)_m(CF_2CF_2)_{l-1}CF_2COF,$$

where its carboxylic acid salt can be formed as an alkali metal salt, or a $NH_4$ salt. The polyfluoroalkane carboxylic acid (or its salt) can act as a surfactant having distinguished monomer emulsifiability and latex stability when used as an emulsifying agent or as a dispersing agent for polymerization reaction of fluorine-containing monomers, or as an effective surfactant capable of enhancing the micelles solubility of fluorine-containing monomers such as vinylidene fluoride, etc., when used as an emulsifying agent or a dispersing agent for homopolymerization or copolymerization reaction of vinylidene fluoride.

9 Claims, No Drawings

POLYFLUORALKANE CARBOXYLIC ACID (OR ITS SALT) AND PROCESS FOR PRODUCING THE SAME

RELATED APPLICATION

This application is a 35 U.S.C. §371 national stage filing of International Patent Application No. PCT/JP2007/064074, filed Jul. 17, 2007, to which priority is claimed under 35 U.S.C. §120 and through which and to which priority is claimed to Japanese Priority Patent Application No. 2006-231587, filed Aug. 29, 2006.

TECHNICAL FIELD

The present invention relates to a polyfluoroalkane carboxylic acid (or its salt) and a process for producing the same, and more particularly to a polyfluoroalkane carboxylic acid (or its salt) for use as an effective surfactant at the time of polymerization reaction of fluorine-containing monomers, etc. and a process for producing the same.

BACKGROUND ART

Fluorine-containing surfactants represented by the general formula RfCOOM (Rf: a perfluoroalkyl group, and M: an alkali metal, an ammonium group, or a hydrogen atom) have been so far widely used in the emulsion polymerization of fluorine-containing monomers, among which perfluorooctanoic acid (or its salt) $C_7F_{15}COOM$ as one of typical surfactants in well known as the most distinguished one, because of its good monomer emulsifiability and latex stability, and easy washability following the salting-out operation.

However, it has been so far clarified that the perfluorinated compounds are hard to decompose in the natural environments, and perfluorooctanoic acid (or its salt) as a typical perfluorinated $C_8$ compound considerably remains in human bodies. It is expectable that an environmental decomposability can be given by forming hydrogenated portions in the perfluorinated hydrophobic groups of the surfactant compound. To decrease the amount of remaining the decomposates in the environments, it is also a desirable that the hydrophobic group must contain a hydrocarbon chain so as to limit a succession of the perfluorinated carbon atoms to less than 8 carbon atoms such as $RfC_mH_{2m}C_nF_{2n}$— (Rf: a perfluoroalkyl group having 1 to 7 carbon atoms, n: an integer of 1 to 7, and m: an integer of 1 or more).

As to the behavior of surfactants at the time of emulsion polymerization reaction, it has been so far proposed to use a perfluoroalkylethane sulfonic acid (or its salt) $F(CF_2CF_2)_n CH_2CH_2SO_3M$ (M: a monovalent cation, and n: 2-8) as a dispersing agent at the time of tetrafluoroethylene copolymerization, though the dispersing agent compound undergoes chain transfer at the time of polymerization reaction, so that the lowering in the molecular weight of the resulting tetrafluoroethylene copolymers is quite unavoidable.
Patent Literature 1: U.S. Pat. No. 4,380,618

It has been also so far disclosed that partially fluorinated, hydrogen-containing fluorine-based surfactants represented by the general formula $Rf(CH_2)_mRf'$ COOM (Rf: a perfluoroalkyl group or a perfluoroalkoxy group having 3 to 8 carbon atoms, Rf': a linear or branched perfluoroalkylene group having 1 to 4 carbon atoms, M: $NH_4$, Li, Na, K or H; and m: an integer of 1 to 3) are used in the polymerization of fluorinated monomers as a hydrogen-containing fluorine-based surfactant having a low chain transferability at the time of polymerization reaction to increase the molecular weight in the homopolymerization of tetrafluoroethylene.
Patent Literature 2: JP-A-10-212261

Such hydrogen-containing fluorine-based surfactant compounds are synthesized by subjecting fluoroalkylethylene or fluoroalkoxyethylene represented by the general formula $Rf(CH_2)_xCH=CX_2$ (X: H or F) to reaction with an iodized ester represented by the general formula $IRf'$ COOR to make iodine-containing intermediates represented by the general formula:

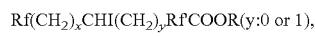
$Rf(CH_2)_xCHI(CH_2)_yRf'COOR(y:0 \text{ or } 1)$, followed by reduction to form esters represented by the general formula:

$Rf(CH_2)_mRf'COOR$.

and further followed by hydrolysis with a base and by neutralization with an acid. In a series of these processes, the substrate is inevitably exposed to a basic environment in the alkali hydrolysis step, so that side reactions such as formation of double bonds, etc. by the dehydrofluorination reaction are liable to take place.

When the hydrogen-containing fluorine-based surfactant is used as an emulsifying agent in the polymerization reaction of fluorine-containing monomers, the monomer emulsificability and latex stability are not better than those by the emulsifying agent of perfluorooctanoic acid (or its salt). Furthermore, when that surfactant is used as an emusifying agent in the homopolymerization or copolymerization reaction of vinylidene fluoride, the micelles solubility of vinylidene fluoride as monomers is so low that the polymerization reaction is not only much retarded, but also the latex stability of the resulting polymers is so low that sometimes the polymers are liable to deposit during the polymerization reaction.

DISCLOSURE OF THE INVENTION

Problem to be Solved by the Invention

The object of the present invention is to provide a polyfluoroalkane carboxylic acid (or its salt) for use as an effective surfactant having distinguished monomer emulsificability and latex stability, when used in the polymerization reaction of fluorine-containing monomers as an emulsifying agent or a dispersing agent, or for use as an effective surfactant capable of enhancing the micelles solubility of fluorine-containing monomers such as vinylidene fluoride, etc., when used as an emulsifying agent or a dispersing agent in the homopolymerization or copolymerization reaction of vinylidene fluoride, and also to provide a process for producing the same.

Means for Solving the Problem

The present invention provides a polyfluoroalkane carboxylic acid, or its salt represented by the following general formula:

$$C_nF_{2n+1}(CH_2CF_2)_m(CF_2CF_2)_{l-1}CF_2COOM \quad [I]$$

(where M is an alkali metal, an ammonium group or a hydrogen atom, n is an integer of 1 to 6, m is an integer of 1 to 4, and l is 1 or 2). The polyfluoroalkane carboxylic acid can be produced by hydrolysis reaction of a polyfluoroalkane carboxylic acid fluoride represented by the following general formula:

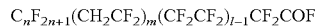
$$C_nF_{2n+1}(CH_2CF_2)_m(CF_2CF_2)_{l-1}CF_2COF \quad [II]$$

(where n is an integer of 1 to 6, m is an integer of 1 to 4, and l is 1 or 2), and its carboxylic acid salt can be formed as an alkali metal salt or an ammonium salt according to the conventional process.

Effect of the Invention

The present polyfluoroalkane carboxylic acid (or its salt) comprises a perfluoroalkyl group having 1 to 6 carbon atoms, so not only its decomposates can be kept to remain much less in the environments, but also the presence of unfluorinated hydrocarbon (—$CH_2$—) sequence can help to produce decomposates of shorter chain length than that of perfluorooctanoic acid (or its salt), when decomposed in the environment or metabolized in the human bodies, and thus can be used as a fluorine-containing surfactant having a low retainability in the environments or human bodies.

When the present polyfluoroalkane carboxylic acid is used in the form of a salt as an emulsifying agent for emulsion polymerization reaction of fluorine-containing monomers or as a dispersing agent for their suspension polymerization reaction, the presence of vinylidene fluoride —$CH_2CF_2$— sequence in the structure of hydrophobic group can help to attain higher emulsion stability of monomers and latex stability or to enhance the micelles solubility of fluorine-containing monomers such as vinylidene fluoride and to accelerate the polymerization reaction, thereby enabling production of fluorine-containing polymers of higher molecular weight. Particularly in the homopolymerization of vinylidene fluoride having a high ability to eliminate hydrogen, lowering of the molecular weight by chain transfer is not found.

BEST MODES FOR CARRYING OUT THE INVENTION

Polyfluoroalkane carboxylic acid (or its salt) represented by the general formula [I] can be produced as a carboxylic acid by hydrolysis reaction of polyfluoroalkane carboxylic acid fluoride represented by the general formula [II], where its salt can be formed as an alkali metal salt or an ammonium salt from the carboxylic acid according to the conventional process.

Polyfluoroalkane carboxylic acid fluoride [II] for use as a raw material in the reaction can be produced by oxidation reaction of a terminally iodized polyfluoroalkane represented by the following general formula:

$$C_nF_{2n+1}(CH_2CF_2)_m(CF_2CF_2)_tI \qquad [III]$$

with an oxidizing agent. The terminally iodized polyfluoroalkane [III] can be produced by reaction of a terminally iodized polyfluoroalkane represented by the following general formula:

$$C_nF_{2n+1}(CH_2CF_2)_m(CF_2CF_2)_tI \qquad [IV]$$

with tetrafluoroethylene in the presence of a peroxide initiator, preferably a peroxide initiator decomposable at low temperatures, at 80° C. or lower.

In the general formula of the terminally iodized polyfluoroalkane [III] obtained by the reaction of the terminally iodized polyfluoroalkane [IV] with tetrafluoroethylene, l=t+r, where t is 0 or a positive integer, which shows the number of tetrafluoroethylene skeletons in the starting raw material, and r is a positive integer, which shows the number of tetrafluoroethylene skeletons as added by the reaction. In the present invention, the tetrafluoroethylene skeletons whose l is preferably 1 or 2 can be used with the skeletons being separated one from another.

Polyfluoroalkane carboxylic acid fluoride [II] having the following general formula:

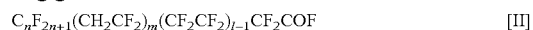

$$C_nF_{2n+1}(CH_2CF_2)_m(CF_2CF_2)_{l-1}CF_2COF \qquad [II]$$

can be formed by oxidation reaction of the terminally iodized polyfluoroalkane [III] with an oxidizing agent, for example, such as fuming sulfuric acid, fuming nitric acid, preferably fuming sulfuric acid. For example, in the case of fuming sulfuric acid comprising concentrated sulfuric acid and about 20 to about 60% of $SO_3$ as absorbed therein to act as an oxidizing agents, the oxidation reaction can be carried out at about 50° to about 100° C. for about 12 to about 48 hours by slowly dropwise adding about 1 to about 10 parts by equivalent weight, preferably about 1.2 to about 6 parts by equivalent weight of fuming sulfuric acid in terms of $SO_3$ to the compound [III]. After the completion of the reaction, the reaction mixture is cooled and left to stand to separate an organic phase containing carboxylic acid fluoride as the major portion from an inorganic phase containing fuming sulfuric acid as the major portion. The organic phase is then rectified by distillation to obtain high purity carboxylic acid fluoride [II].

Hydrolysis reaction of the resulting carboxylic acid fluoride [II] can be readily carried out by adding water or an aqueous solution of water-soluble organic solvent, or the like thereto. The resulting polyfluoroalkane carboxylic acid can be readily converted to an alkali metal salt or an ammonium salt through contact with an aqueous solution of potassium hydroxide, an aqueous solution of sodium hydroxide, an aqueous solution of lithium hydroxide, an aqueous ammonia solution, or the like.

The present polyfluoroalkane carboxylic acid salt can be used as a suitable emulsifying agent for the emulsion polymerization reaction of fluorine-containing monomers, or as a suitable dispersing agent for the suspension polymerization reaction thereof. For example, when the present surfactant is used in the polymerization reaction of vinylidene fluoride, the amount of vinylidene fluoride dissolvable into the aqueous surfactant solution can be increased.

The fluorine-containing monomers for the emulsion polymerization or suspension polymerization in the presence of the present surfactant include, for example, vinylidene fluoride, tetrafluoroethylene, hexafluoropropylene, chlorotrifluoroethylene, trifluoroethylene, vinyl fluoride, perfluoro(alkyl vinyl ether) having an alkyl group having 1 to 3 carbon atoms, etc. One or two or more kinds of these fluorine-containing monomers can be used in the polymerization reaction to form homopolymers or copolymers. The fluorine-containing monomers can be used to form copolymers with fluorine-free monomers, for example, propylene, ethylene, etc.

In the polymerization reaction, the present surfactant can be used as an emulsifying agent for the emulsion polymerization reaction, or as a dispersing agent for the suspension polymerization, in a proportion of about 0.05 to about 5% by weight, preferably about 0.2 to about 1% by weight, on the basis of water or an aqueous medium containing water-soluble alcohol, etc. The polymerization reaction can be carried out preferably in the presence of a water-soluble polymerization initiator, or a redox polymerization initiator formed therewith. The resulting reaction mixture can be coagulated with an aqueous solution of metal salt, followed by water washing and drying to obtain homopolymers or copolymers of desired fluorine-containing monomers.

EXAMPLES

The present invention will be described in detail below, referring to Examples.

Reference Example 1

Synthesis Example of Raw Material Compound 600 g of $CF_3(CF_2)_3(CH_2CF_2)I$ $[C_6F_{11}H_2I]$ (purity: 99.5%) was charged into an autoclave having a capacity of 1,200 ml, and heated to an inside temperature of 50° C. Then, 1.35 g of a peroxide-based initiator (Percadox 16, a product of Kayaku-Akuzo Co.) as dissolved in 300 g of $C_6F_{11}H_2I$ was added thereto. When the inside temperature reached 55° C., tetrafluoroethylene was portionwise-added thereto, while keeping the pressure at 0.2-0.3 MPa. When the portionwise-addition reached to 150 g, aging was carried out at 55°-74° C. for one hour to complete the reaction. After the completion of the reaction, cooling was conducted to recover 1010 g of the product as a mixture.

Analytical results of the product by gas chromatography (GC) are given in the following Table 1 as GC % of a compound represented by the following general formula having various values of n, m, and l(t+r), where the remaining 1.7 GC % shows impurities of unidentified structures:

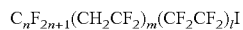

$C_nF_{2n+1}(CH_2CF_2)_m(CF_2CF_2)_lI$

TABLE 1

| n | m | l(t + r) | Raw material | Product |
|---|---|----------|--------------|---------|
| 4 | 1 | 0 | 99.5 | 44.7 |
| 4 | 1 | 1 |  | 37.1 |
| 4 | 1 | 2 |  | 12.0 |
| 4 | 1 | 3 |  | 3.5 |
| 4 | 1 | 4 |  | 0.8 |
| 4 | 1 | 5 |  | 0.2 |

Among the afore-mentioned reaction mixture (product), a compound (n=4, m=1, and l=1) was isolated, therefrom by distillation (boiling point 54° C./0.4 kPa) and used as a raw material in Example 1.

Reference Example 2

Synthesis Example of Raw Material Compound

In Reference Example 1, the raw material and the initiator solvent were changed to the same species of $CF_3(CF_2)_3(CH_2CF_2)_2I$ (purity: 99.7%), and the amount of portionwise-added tetrafluoroethylene was changed to 210 g, whereby 1075 g of a product was recovered as a mixture.

Analytical results of the resulting product by gas chromatography (GC) are shown in the following Table 2 by GC % of a compound represented by the following general formula having various values of n, m, and l(t+r), where the remaining 1.1 GC % shows impurities having unidentified structures:

$C_nF_{2n+1}(CH_2CF_2)_m(CF_2CF_2)_lI$

TABLE 2

| n | m | l(t + r) | Raw material | Product |
|---|---|----------|--------------|---------|
| 4 | 2 | 0 | 99.7 | 12.1 |
| 4 | 2 | 1 |  | 32.2 |
| 4 | 2 | 2 |  | 45.8 |
| 4 | 2 | 3 |  | 8.8 |

Among the afore-mentioned reaction mixture (product), a compound (n=4, m=2, and l=2) was isolated therefrom by distillation (boiling point: 88°-92° C./0.4 kPa), and used as a raw material in Example 4.

Example 1

30 g of $CF_3(CF_2)_3(CH_2CF_2)(CF_2CF_2)I$ (purity: 99.8%) was charged into a glass reactor having a capacity of 200 ml, and 90 g of fuming sulfuric acid containing 30 wt. % $SO_3$ as absorbed therein (in a ratio of $SO_3$ to raw material compound by equivalent: 5.8) was slowly dropwise-added thereto. The reactor was then heated to 60° C. to conduct reaction for about 24 hours. After the completion of reaction, the reaction mixture was cooled and left to stand to separate an organic phase containing carboxylic acid fluoride as the major portion from an inorganic phase containing fuming sulfuric acid as the major portion. Then, about 10 g of the organic phase was rectified by distillation to obtain 3.2 g of high purity carboxylic acid fluoride $CF_3(CF_2)_3(CH_2CF_2)CF_2COF$ having a boiling point of 60° C./13.5 kPa (yield: 27% and purity: 97%).

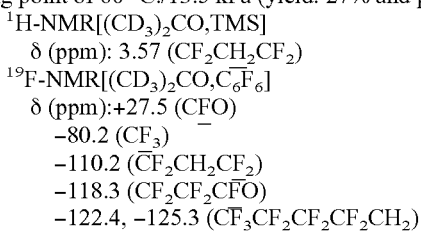

$^1H$-NMR$[(CD_3)_2CO,TMS]$
  $\delta$ (ppm): 3.57 ($CF_2\underline{CH_2}CF_2$)
$^{19}F$-NMR$[(CD_3)_2CO,C_6\underline{F}_6]$
  $\delta$ (ppm): +27.5 ($\underline{C}FO$)
    −80.2 ($\underline{CF_3}$)
    −110.2 ($\underline{CF_2}CH_2CF_2$)
    −118.3 ($CF_2\underline{CF_2}CFO$)
    −122.4, −125.3 ($\underline{CF_3CF_2CF_2}CF_2CH_2$)

Carboxylic acid $CF_3(CF_2)_3(CH_2CF_2)CF_2COOH$ was quantitatively obtained by adding water to the carboxylic acid fluoride, followed by stirring.

$^1H$-NMR$[(CD_3)_2CO,TMS]$
  $\delta$(ppm): 3.45 ($CF_2\underline{CH_2}CF_2$)
    13.8 ($CF_2COO\underline{H}$)
$^{19}F$-NMR$[(CD_3)_2CO,C_6\underline{F}_6]$

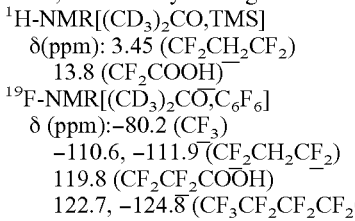

$\delta$ (ppm): −80.2 ($\underline{CF_3}$)
    −110.6, −111.9 ($\underline{CF_2}CH_2\underline{CF_2}$)
    119.8 ($CF_2\underline{CF_2}COOH$)
    122.7, −124.8 ($\underline{CF_3CF_2CF_2}CF_2CH_2$)

Ammonium carboxylate $CF_3(CF_2)_3(CH_2CF_2)CF_2COONH_4$ was likewise quantitatively obtained by adding an aqueous 25 wt. % ammonia solution to the carboxylic acid, followed by stirring.

Example 2

Vinylidene fluoride was introduced into a stainless steel autoclave having a capacity of 1 L, provided with a stirrer, while keeping the autoclave inside temperature at 40° C., until the pressure reached 30 kgf/cm²·G (2.94 MPa·G). The amount of vinylidene fluoride introduced by that time was 74.7 g, which corresponded to 37.3 g in terms of reactor space volume of 500 ml. Then, the autoclave was degasified, and 500 ml of an aqueous solution containing 2.8 g of the ammonium carboxylate obtained in the foregoing Example 1 was charged therein. Then, vinylidene fluoride was introduced into the autoclave with stirring, while keeping the autoclave inside temperature at 40° C., until the pressure reached 30 kgf/cm²·G (2.94 MPa·G). The amount of vinylidene fluoride introduced by that time was 69.9 g. It was presumed that there must be 37.3 g of vinylidene fluoride in the autoclave space of 500 ml as not filled with the solution. The amount of vinylidene fluoride dissolved in the aqueous solution of the ammonium carboxylate under that temperature and pressure condition was 32.6 g (=69.9 g−37.3 g) by calculation.

The amount of vinylidene fluoride dissolved in water without using the ammonium carboxylate under the same temperature and pressure condition was 30.0 g. The amount of vinylidene fluoride dissolved in an aqueous solution containing ammonium perfluorooctanoate $C_7F_{15}COONH_4$ in place of the ammonium carboxylate was 28.8 g under the same temperature and pressure condition.

Example 3

550 ml of water, 1.2 g of Na$_2$HPO$_4$, 0.12 g of isopropanol, and 2.8 g of ammonium carboxylate obtained in the foregoing Example 1 were charged into a stainless steel autoclave having a capacity of 1 L, provided with a stirrer, and degasified, then vinylidene fluoride was introduced therein with stirring, while keeping the autoclave inside temperature at 80° C., until the pressure reached 25 kgf/cm$^2$·G (2.45 MPa·G).

Then, 0.24 g of ammonium persulfate dissolved in 50 ml of water was charged therein to initiate polymerization reaction. During the polymerization reaction, vinylidene fluoride was additionally introduced therein to keep the autoclave inside pressure at 24-25 kgf/cm$^2$·G (2.35-2.45 MPa·G). At 108 minutes after the charging the polymerization initiator, and when sum total of introduced vinylidene fluoride reached 220 g, the autoclave was cooled to discontinue the emulsion polymerization reaction, and an aqueous 0.5 wt. % MgCl$_2$ solution was added to the reaction mixture to effect coagulation.

The resulting solid polymers were washed with distilled water, recovered by filtration, and vacuum dried at 80° C. to obtain 190 g of vinylidene fluoride homopolymers. The vinylidene fluoride homopolymers were extruded through a melt index tester at 230° C. under a weight of 5 kg at an extrusion rate of 0.123 g/10 min. Intrinsic viscosity [η] of the vinylidene fluoride homopolymers at 35° C. in dimethyl formamide was 1.68.

Reference Example 3

Reference Polymerization Example Using C$_7$F$_{15}$COONH$_4$)

In Example 3, the same amount of ammonium perfluorooctanoate C$_7$F$_{15}$COONH$_4$ was used as an ammonium carboxylate, and the duration of introducing vinylidene fluoride was changed to 113 minutes (220 g), whereby 188 g of vinylidene fluoride homopolymers were contained. The vinylidene fluoride homopolymers had an extrusion rate of 0.152 g/10 min. and an intrinsic viscosity [η] of 1.49.

Example 4

In Example 1, the same amount of CF$_3$(CF$_2$)$_3$(CH$_2$CF$_2$)$_2$(CF$_2$CF$_2$)$_2$I was used in place of CF$_3$(CF$_2$)$_3$(CH$_2$CF$_2$)(CF$_2$CF$_2$)I and the amount of the fuming sulfuric acid containing 30 wt. % SO$_3$ as absorbed therein was changed to 70 g (ratio of SO$_3$ to raw material compound by equivalent 6) to conduct synthesis reaction. 7.9 g of CF$_3$(CF$_2$)$_3$(CH$_2$CF$_2$)$_2$(CF$_2$CF$_2$)CF$_2$COF having a boiling point of 93° C./13.5 kPa was obtained (yield: 28%).

The carboxylic acid fluoride was admixed with water with stirring, whereby carboxylic acid CF$_3$(CF$_2$)$_3$(CH$_2$CF$_2$)$_2$(CF$_2$CF$_2$)CF$_2$COOH was quantitatively obtained. The carboxylic acid was admixed with a aqueous 25 wt. % ammonia solution with stirring, whereby ammonium carboxylate CF$_3$(CF$_2$)$_3$(CH$_2$CF$_2$)$_2$(CF$_2$CF)CF$_2$COONH$_4$ was quantitatively obtained.

Example 5

In Example 2, the ammonium carboxylate obtained in Example 4 was used as an ammonium carboxylate, where the amount of vinylidene fluoride dissolved in an aqueous solution of ammonium carboxylate was found 30.8 g.

The invention claimed is:

1. A polyfluoroalkane carboxylic acid or its salt, represented by the following general formula:

$$C_nF_{2n+1}(CH_2CF_2)_m(CF_2CF_2)_{l-1}CF_2COOM \quad [I]$$

(where M is an alkali metal, an ammonium group or a hydrogen atom, n is an integer of 1 to 6, m is an integer of 1 to 4, and l is 1 or 2).

2. A polyfluoroalkane carboxylic acid or its salt according to claim 1, for use as an emulsifying agent for emulsion polymerization reaction of fluorine-containing monomers, or as a dispersing agent for suspension polymerization reaction thereof.

3. A polyfluoroalkane carboxylic acid fluoride represented by the following general formula:

$$C_nF_{2n+1}(CH_2CF_2)_m(CF_2CF_2)_{l-1}CF_2COF \quad [II]$$

(where n is an integer of 1 to 6, m is an integer of 1 to 4, and l is 1 or 2).

4. A process for producing a polyfluoroalkane carboxylic acid represented by the following general formula:

$$C_nF_{2n+1}(CH_2CF_2)_m(CF_2CF_2)_{l-1}CF_2COOH \quad [I']$$

(where n is an integer of 1 to 6, m is an integer of 1 to 4, and l is 1 or 2) which process comprises subjecting a polyfluoroalkane carboxylic acid fluoride [II] according to claim 3 to hydrolysis reaction.

5. A process for producing a polyfluoroalkane carboxylic acid fluoride according to claim 3, which process comprises subjecting a terminally iodized polyfluoroalkane represented by the following general formula:

$$C_nF_{2n+1}(CH_2CF_2)_m(CF_2CF_2)_lI \quad [III]$$

(where n is an integer of 1 to 6, m is an integer of 1 to 4, and l is 1 or 2) to oxidation reaction by an oxidizing agent.

6. A process for producing a polyfluoroalkane carboxylic acid fluoride according to claim 5, wherein the oxidizing agent is fuming sulfuric acid.

7. A polyfluoroalkane carboxylic acid or its salt according to claim 1, represented by the following general formula:

$$C_nF_{2n+1}(CH_2CF_2)CF_2COOM$$

(where M is an alkali metal, an ammonium group, or a hydrogen atom, and n is an integer of 1 to 6).

8. A polyfluoroalkane carboxylic acid or its salt according to claim 1 represented by the following general formula:

$$C_nF_{2n+1}(CH_2CF_2)_2(CF_2CF_2)CF_2COOM$$

(where M is an alkali metal, an ammonium group, or a hydrogen atom and n is an integer of 1 to 6).

9. A polyfluoroalkane carboxylic acid or its salt according to claim 2, wherein the fluorine-containing monomers are vinylidene fluoride.

* * * * *